United States Patent [19]

Newell et al.

[11] Patent Number: 4,778,054

[45] Date of Patent: Oct. 18, 1988

[54] PACK FOR ADMINISTERING MEDICAMENTS TO PATIENTS

[75] Inventors: Robert E. Newell, Pinner; Robert A. Fitzsimmons, Barnard Castle, both of England

[73] Assignee: Glaxo Group Limited, London, England

[21] Appl. No.: 936,148

[22] Filed: Dec. 1, 1986

Related U.S. Application Data

[63] Continuation-in-part of Ser. No. 540,203, Oct. 7, 1983, Pat. No. 4,627,432.

[30] Foreign Application Priority Data

Oct. 8, 1982 [GB] United Kingdom ............... 8228887
May 25, 1983 [GB] United Kingdom ............... 8314307

[51] Int. Cl.⁴ ............................................. B65D 83/04
[52] U.S. Cl. ................................. 206/531; 206/532; 206/469; 206/538; 206/540
[58] Field of Search ............... 206/469, 531, 532, 538, 206/540

[56] References Cited

U.S. PATENT DOCUMENTS

| | | | |
|---|---|---|---|
| 4,015,717 | 4/1977 | Richardson et al. | 206/531 |
| 4,074,806 | 2/1978 | Ardito | 206/531 |
| 4,089,415 | 5/1978 | Laib. | |
| 4,298,125 | 11/1981 | Berghahn | 206/531 |
| 4,342,395 | 8/1982 | Brown. | |

FOREIGN PATENT DOCUMENTS

| | | |
|---|---|---|
| 516834 | 7/1938 | United Kingdom. |
| 925927 | 6/1961 | United Kingdom. |
| 1019963 | 10/1962 | United Kingdom. |
| 1075679 | 12/1963 | United Kingdom. |
| 1387959 | 5/1973 | United Kingdom. |

Primary Examiner—Joseph Man-Fu Moy
Attorney, Agent, or Firm—McAulay, Fields, Fisher, Goldstein & Nissen

[57] ABSTRACT

A pack is provided comprising a circular carrier disc provided with a plurality of containers arranged in a circle and each containing a dose of medicament in particulate form. The containers are puncturable to permit the medicament therein to be released.

15 Claims, 6 Drawing Sheets

PACK FOR ADMINISTERING MEDICAMENTS TO PATIENTS

RELATED APPLICATION

This application is a continuation-in-part of U.S. Ser. No. 540,203 filed 10/07/83 and now U.S. Pat. No. 4,627,432 entitled "Devices for Administering Medicaments to Patients".

FIELD OF THE INVENTION

This invention relates to a medicament-containing pack for use in a device by means of which the medicament can be administered to or by patients inhaling through the device. The medicament is in powder form.

BACKGROUND OF THE INVENTION

Devices are now quite well known for administering medicaments contained in capsules to patients suffering from bronchial conditions such as, for example, bronchial asthma. It is well known for medicament in powder or other finely divided form to be supplied in capsules which are loaded by a patient into such a device. The medicament is then released from the capsule and inhaled by the patient, usually through the mouth, but sometimes through the nose.

The specifications of PCT Application Publication No. WO82/01470 and U.K. Patent Specification No. 1387954 both describe devices for dispensing medicament in powder form from capsules. In each of these previously described devices, the capsules are mounted on a rotatable support member on which each capsule in turn can be brought to a position in which it is opened to enable medicament to exit from the capsule to permit it to be inhaled by a patient inhaling through a mouthpiece of the device. In the device described in U.K. Specification No. 1387954, the capsules may be mounted in a so-called blister pack.

There are disadvantages in the use of capsules, which are made of gelatin, to contain medicaments. Gelatin is relatively unstable and is lacking in physical strength so that the capsules need to be protected by packaging, for example in glass bottles. Environmental degradation of both the capsules and their contents may occur in a relatively short time.

BRIEF SUMMARY OF THE INVENTION

An object of the present invention is to provide a more convenient way of administering medicament to such patients than has been possible hitherto and which avoids the need to pack medicaments in capsules. The present invention preferably makes use of the technique of packing medicaments by loading them in blister packs, that is to say packs comprising a-sheet, which may be laminated, of foil or plastics material which acts as a carrier and which is provided with a number of breakable or openable containers called "blisters" incorporating a sheet secured on a first sheet to form a cover or lid. Such blister packs are in common use with tablets of one kind or another, but we have discovered that they can also be used with medicaments in powder form.

According to the present invention there is provided a pack comprising a circular carrier disc which has a plurality of pre-filled, hermetically sealed containers formed integrally therewith and arranged in a circle, each container containing directly a dose of medicament in the form of a powder, each container being puncturable to form a hole on each side thereof to allow air to flow through the container to entrain the powder contained therein.

The invention is suitable for administering a variety of medicaments such as, for example, salbutamol, beclomethasone dipropionate and sodium cromoglycate.

BRIEF DESCRIPTION OF THE DRAWINGS

The accompanying schematic drawings show some devices in which a pack according to the invention may be used, as well as the pack itself.

DETAILED DESCRIPTION OF PREFERRED EMBODIMENTS

Figure 1:
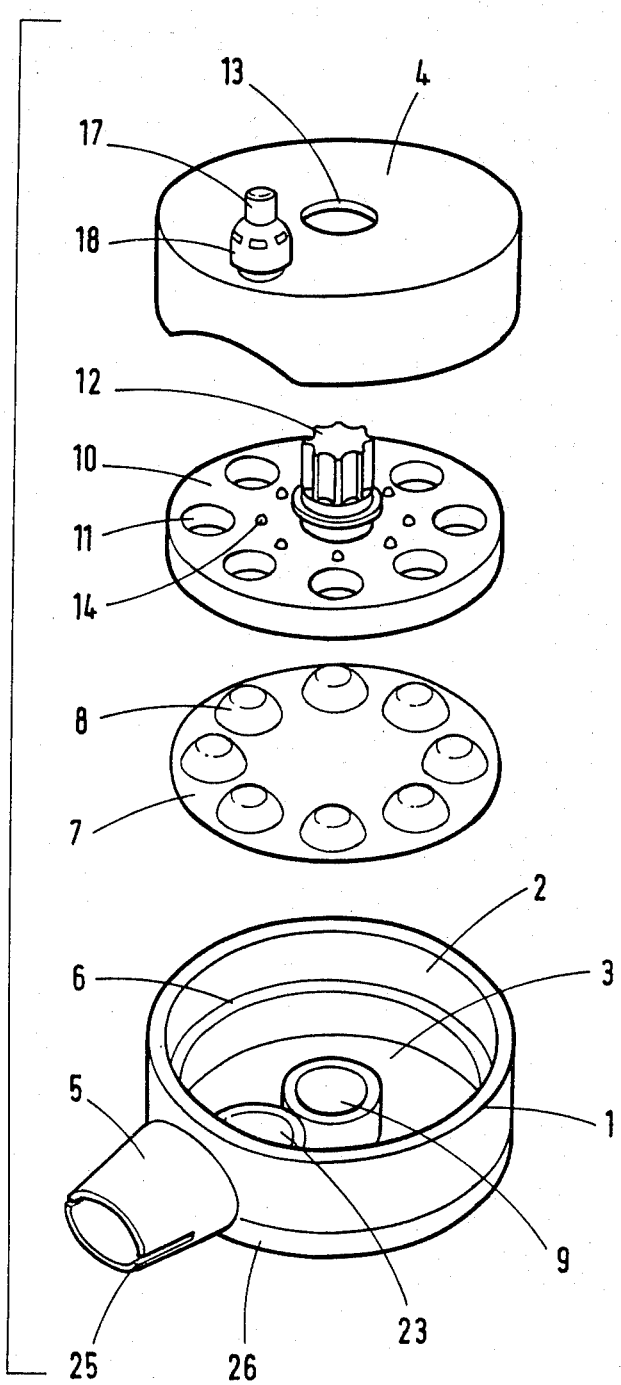
FIG. 1 is an exploded perspective view of a first embodiment of the device.
Figure 2:
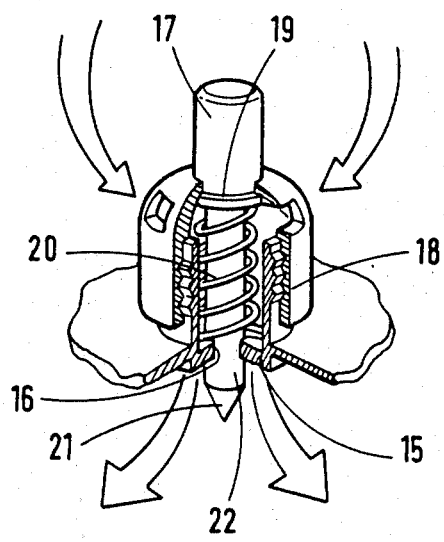
FIG. 2 is a detailed view of a plunger device of the same device.

The device illustrated in FIGS. 1 and 2 of the drawings comprises a shallow cylindrical housing 1 of a plastics material which has a cylindrical chamber 2 therein. The chamber is closed at one end 3, herein considered the bottom of the chamber, and a removable cover 4 is a close fit over the chamber at the other end.

A mouthpiece outlet 5 projects outwardly from the cylindrical wall of the housing 1 and communicates with the interior of the chamber 2. A perforated guard, not shown, is provided in the mouthpiece to prevent any solid particles of an undesirably large size being inhaled by a patient inhaling through the mouthpiece.

A rim or shoulder 6 runs round the inside wall of the chamber 2 to provide an annular support on which a blister pack 7 may be located. The blister pack has a plurality of puncturable containers or "blisters" 8 arranged in a circle. The blisters 8 are filled with medicament in the form of a powder.

The blister pack is of circular disc form, and is removably fitted inside the chamber so that it is replaceable when the individual doses of medicament contained in the blisters have been discharged. The blister pack 7 is preferably a circular disc of foil laminate material with blisters or containers 8. Further details of the blister pack are given in the ensuing description.

The chamber 2 contains a central open cylindrical support column 9 upstanding from the bottom wall 3 of the chamber. A clamp disc member 10 is removably fitted inside the chamber 2 and is rotatable therein. In use, the clamp member is placed on top of a blister pack 7 which has already been loaded into the chamber and is located on the support shoulder 6.

The clamp member 10 has a plurality of apertures 11 which are arranged in a circle and so spaced from each other that each of them will receive one of the blisters 8 of the blister pack 7. A knob 12 is upstanding from the clamp member 10 and when the lid 4 is fitted on the housing 1 the knob 12 will project through an aperture 13 in the top of the lid 4. This knob can be turned by the patient to rotate the clamp member 10 and since the blisters 8 of the blister pack 7 are located in the apertures 11 in the clamp plate 10 rotation of the clamp member will also rotate the blister pack. A plurality of protuberances or pips 14 are provided on the top of the clamp member 10 and engage in a recess 15, FIG. 2, on the underside of the cover 4 to make sure that the clamp plate is correctly aligned in position. As will be seen, the knob 12 is fluted to provide a better grip for the patient.

The cover 4 also has an aperture 16 in which a plunger 17 contained in a plunger housing 18 can be received. The plunger has an annular shoulder 19 and a spring 20 can bear between the shoulder 19 and the bottom of the plunger housing 18 to urge the plunger into an upper or inoperative position. The plunger may be provided with a knife edge 21 or other means to enable the blister to be punctured more easily. When the plunger 17 is depressed against the action of the spring 20, the lower edge portion 21 of the plunger will pass through an aperture 22 in the plunger housing to pass through a blister 8 located in register with the plunger. Such engagement will puncture the blister, forming a hole on both sides thereof. This action will so open the blister that when a patient inhales air will pass through the blister, the medicament being entrained in the air flow and exiting through the mouthpiece 5 via a transfer cavity 23 inside the chamber in communication with the mouthpiece 5. By rotation of the knob 12 the clamp member 10 and the blister pack 7 can be rotated to bring each blister in turn into location beneath the plunger. The various protuberances or pips 14 will in turn engage in the recess 15 to make sure that the blister pack is correctly registered with the plunger.

It is not essential that the plunger have a knife 21 to puncture the blister. If desired a needle can be used to puncture the blister or the plunger may have a pointed end or even a blunt end or any other convenient puncturing means may be used.

The mouthpiece cover can have a locking member (not shown) which can be engaged with the plunger when the device is not in use to prevent accidental actuation of the plunger.

In use, the patient needing a dose of medicament may hold the device with the mouthpiece in his mouth. The patient then depresses the plunger to puncture the blister and give access to the medicament therefrom and inhales through the mouthpiece so that the medicament will be entrained in the air flow and will enter the lungs of the patient. If desired, the mouthpiece can be provided with air inlet slots 25 to modify the air flow as the patient inhales.

In a modification not illustrated the underside of the blister pack can be supported on another clamp plate instead of the support rim or shoulder 6.

The blister pack is conveniently arranged to provide a sufficient number of individual doses for a patient for use during a convenient period such as one day or more.

The housing can be modified by providing an additional chamber, not visible, at the bottom, this additional chamber being closed by a removable cover 26. This additional chamber can be used to store replacement blister packs.

The mouthpiece may, if desired, be arranged so that a patient may use it to inhale through the nose.

Figure 3:
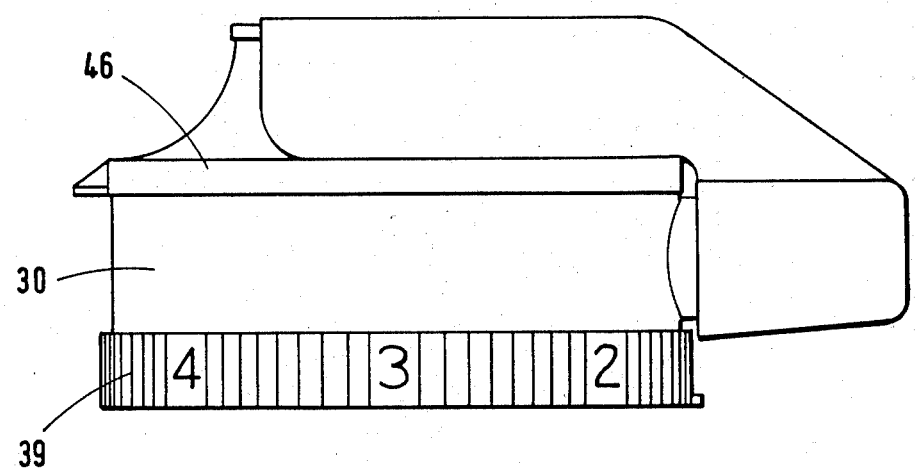
FIG. 3 is an elevation of another embodiment of the device.
Figure 4:
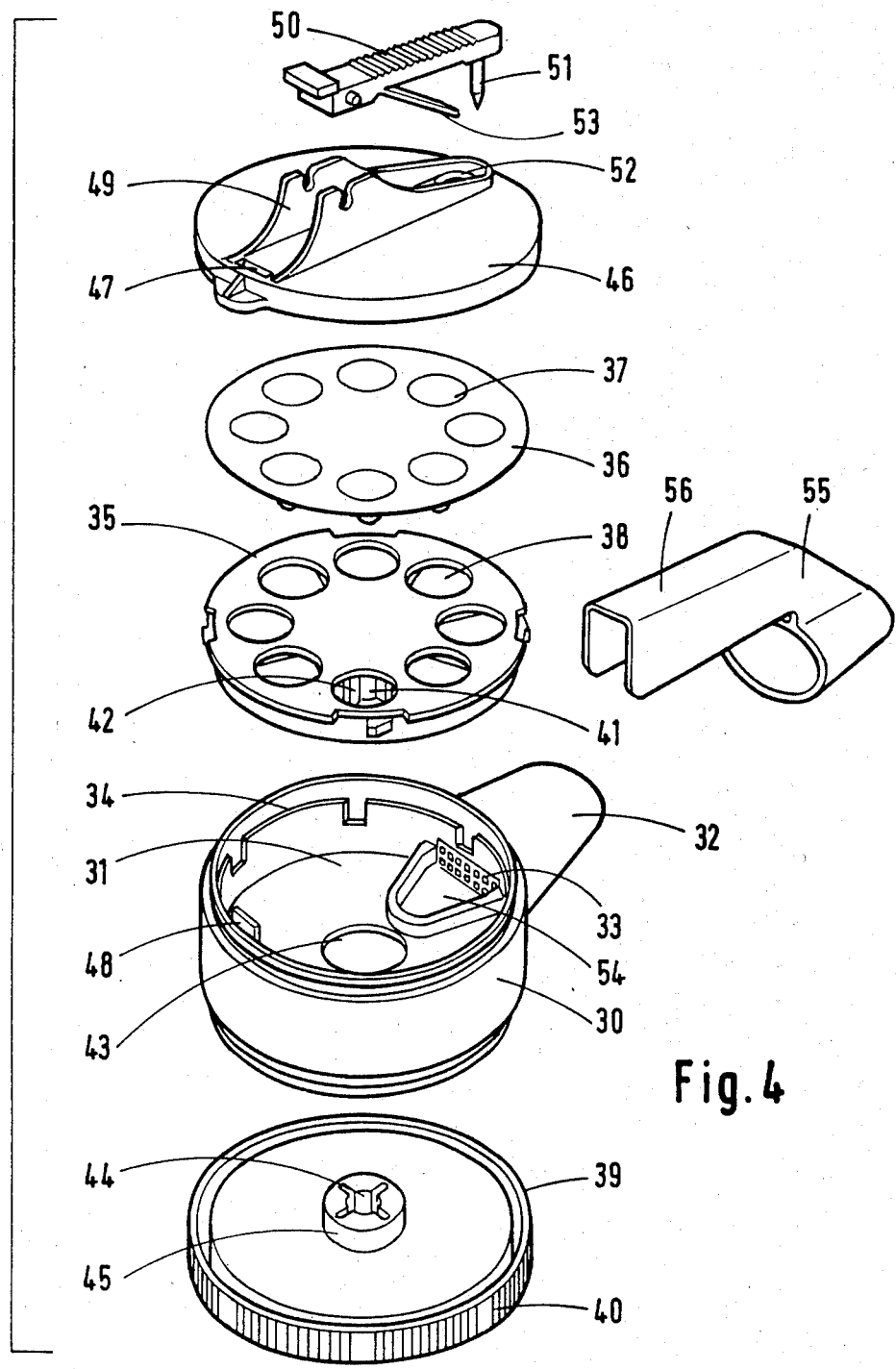
FIG. 4 is an exploded view of the embodiment illustrated in FIG. 3.

A modified device which does not use the clamp member 10 is illustrated in FIGS. 3 and 4. The device of this modification comprises a housing 30 having a chamber 31 therein. A mouthpiece 32 projects outwardly from the cylindrical wall of the housing 30 in a generally radial direction and communicates with the interior of the chamber 31. A perforated guard 33 is provided at the entrance to the mouthpiece 32. A rim or shoulder 34 runs round the inside wall of the chamber 31 to provide an annular support for a support member 35 in the form of a circular plate or disc. This support member is arranged to receive a blister pack 36. The blister pack 36 has a plurality of puncturable containers 37 arranged in a circular row. These containers are in the form of "blisters" of a generally conical form and contain a medicament as described with reference to FIG. 1. The support member 35 has a plurality of holes 38 equal in number to the number of blisters 37 of the blister pack 36. The conical portion of one blister 37 is located in each of the holes 38 when the device is loaded and in use. An external rotatable member 39 with a knurled edge 40 is located in face contact with the bottom of the housing 30. A spindle or the like 41 with radial projections 42 extends centrally from the support member 35 through a hole 43 in the bottom of the housing 30 and into an opening 44 of complementary shape in a spigot 45 of the member 39. The spigot 45 passes through the hole 43 and the spindle 41 and 42 engages in the opening 44 so that rotation of the member 39 will cause similar rotation to the support member 35. A removable cover 46 fits on top of the housing 30. An opening 47 is provided in the cover 46 and engages a projection 48 in the housing 30 so as correctly to locate the cover. The cover 46 carries a bracket 49 on which a lever or trigger 50 is pivotally mounted. A plunger 51 is located on the lever or trigger 50 and extends through a hole 52 in the cover. A spring 53 is provided to bear between the trigger or lever 50 and the top of the cover 46 to urge the lever or trigger upwards.

The hole 52 is so positioned that each hole 38 in the support member 35 will register with this hole as the support member 35 is rotated.

When one of the holes 38 is in register with the hole 52 the trigger 50 can be depressed so that its plunger 51, which may be in the form of a needle, will pierce through the blister 37 located in that hole (i.e. pierce the top and the bottom of the blister) thereby to permit powder to exit from the blister. Some powder will fall into a tray-like compartment 54 inside the chamber 31. When the patient inhales, air passes through the pierced blister so that powder will be entrained in the airflow and will, with powder from the compartment 54, be withdrawn through the guard 33 and the mouthpiece 32. When the device is not in use, the mouthpiece 32 can be enclosed in a mouthpiece cover or sheath 55 which has a channel-like extension 56 which will engage with the bracket 49 to prevent the plunger 51 being depressed to enter through the hole 37.

When the device is in use and the patient inhales through the mouthpiece 32 it is, of course, essential for air to be able to enter the interior of the chamber 31.

Any suitable air inlets can be provided. Conveniently, however, air can enter through the hole 52 the plunger or needle 51 being smaller in diameter than the diameter of the hole 52 so that it serves as an air inlet.

Figure 5:
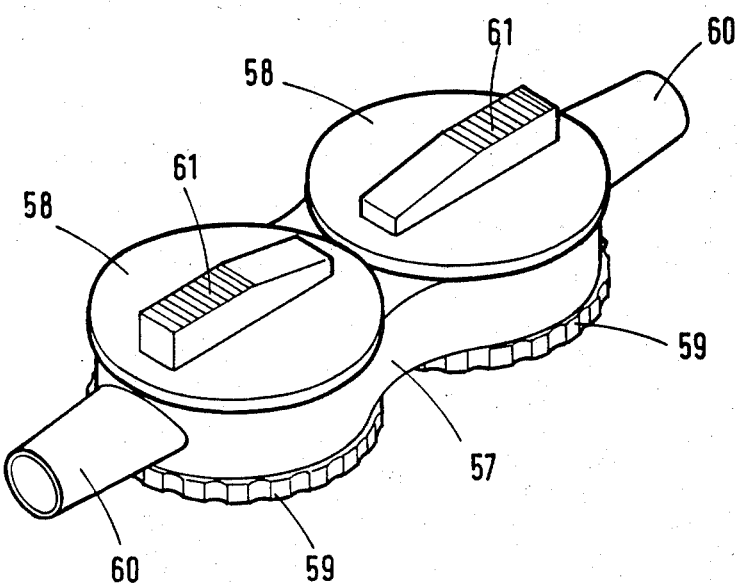
FIG. 5 is a perspective view of yet another device.

FIG. 5 illustrates a modified device which can conveniently be used to administer two different medicaments to a patient at separate times. Treatment of certain patients does require that they inhale two different kinds of medicament. In the device illustrated in FIG. 5, a common housing 57 contains two chambers equivalent to the chamber 2 of the embodiment illustrated in FIGS. 1 and 2 or to the chamber 31 of the embodiment illustrated in FIGS. 3 and 4. These two chambers are enclosed by removable covers 58 and blister packs contained in the chambers can be rotated in the manner previously described by rotation of knurled wheels, knobs or other members 59. Outlet mouthpieces 60 project outwardly from the common housing 57, each one of these outlets 60 leading into one of the chambers enclosed by the common housing. Trigger mechanisms 61 are provided to enable the blisters of the blister packs contained in the chambers to be pierced so that the contents thereof can be inhaled by the patient.

More details of the blister packs which may be used will now be given, with reference to FIGS. 6 to 13 of the accompanying drawings.

Figure 6:
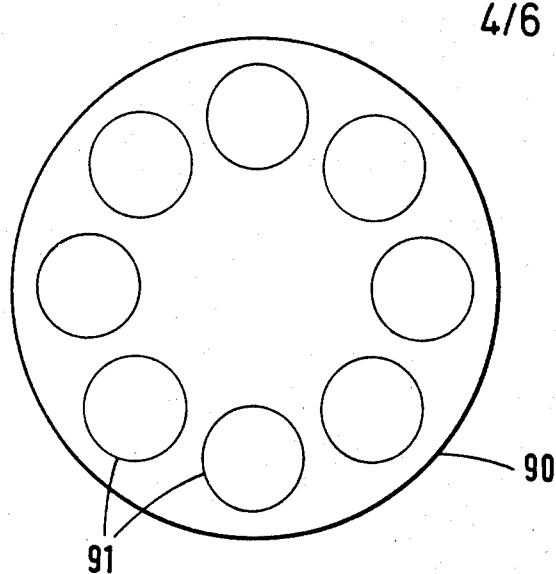
FIG. 6 is a plan view of a blister pack according to the invention.
Figure 7:
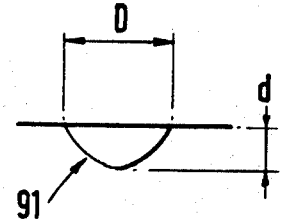
FIG. 7 is a vertical section through a single blister, before puncturing.

FIGS. 6 and 7 show a blister pack 90 which is circular in plan view, and has a plurality of blisters 91, in this case eight such blisters, to contain powdered medicament. The blisters are each circular in plan view and are arranged in a circle, so as to give a blister pack of the same general appearances as the blister pack 7 in FIG. 1 and the blister pack 36 in FIG. 4. Each blister has a diameter D and a depth d. The values which D and d should have are discussed further below. The diameter of the blister pack itself in this case is 54 mm. The smallest distance between adjacent blisters and between any given blister and the outer edge of the blister pack is preferably at least 3 mm in order to provide an adequate seal between the base and lid film which form the blister pack (see below).

The blister pack 90 is formed from a base laminate to which is secured a lid laminate in which the blisters 91 are formed. The example shown in FIG. 8 comprises a base laminate 100, and a lid laminate 110 in which are formed the blisters 91 of which part of one is shown. The blisters each contain powdered medicament 112. The base laminate comprises three principal layers, namely a layer 101 of polyvinyl chloride 100 microns thick which forms one internal surface of each of the blisters and must thus be inert to the medicament 112, a layer 102 of aluminum foil 40 microns thick, and a layer 103 of biaxially oriented polyamide 25 microns thick. The layers are secured to one another by layers of adhesive 104 and 105. As indicated by broken lines, a fourth principal layer 106 may be added, namely a further layer of biaxially oriented polyamide 20 microns thick. This is secured to the layer 103 by an adhesive layer 107. The lid laminate 110 comprises a layer 118 of heat seal lacquer applied at a rate of 9 g/m² which forms an internal surface of each of the blisters and must thus be inert with respect to the medicament 112, a layer 114 of aluminum 25 microns thick and a layer 115 of a polyester lacquer applied at a rate of 2-10 g/m². The lacquer layer 115 can be coloured, for decorative purposes and/or to assist the patient in identifying the medicament, and can also carry printing, for example further identification and/or instructions for use.

The base and lid laminates are impermeable to light, air water and water vapor, and microorganisms, and the heat seal which the lacquer layer 113 forms with the PVC layer 101 is likewise impermeable, so that the medicament 112 is completely protected.

Figure 8:
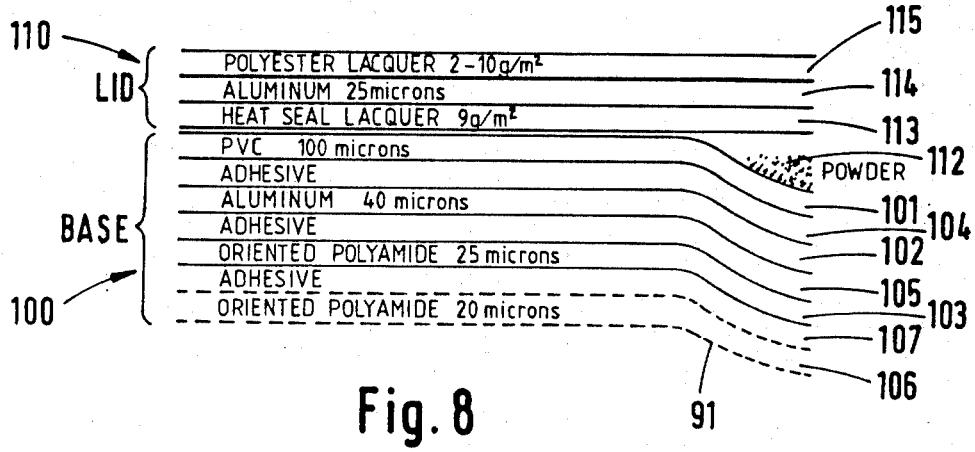
FIGS. 8 and 9 are vertical sections, not to scale, through part of two packs according to the invention, showing examples of materials which may be used.
Figure 9:
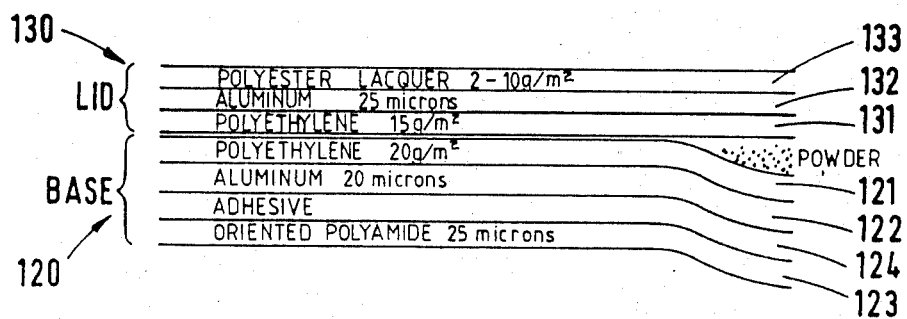

FIG. 9 shows alternative materials which may be used. The blister pack of FIG. 9 comprises a base laminate 120 and a lid laminate 130. The base laminate comprises a polyethylene layer 121 applied at a rate of 20 g/m² and an aluminum layer 122 which is 20 microns thick. In the manufacture of the base laminate the polyethylene is extruded on to the aluminum. The base laminate 120 further comprises a layer 123 of oriented polyamide 25 microns thick secured to the layer 122 by an adhesive layer 124. The lid laminate 180, which is heat sealed to the base laminate, comprises a layer 181 of polyethylene applied at a rate of 15 g/m² extruded on to a layer 132 of aluminum 25 microns thick, and a layer 133 of polyester lacquer applied at a rate of 2-10 gm/m². The lacquer layer 188 serves the same purpose as the lacquer layer 115 in the embodiment of FIG. 8. The layers 121 and 131 of polyethylene from the internal surfaces of the powder-containing blisters and are inert with respect to the powder. The embodiment of FIG. 9 has basically the same impermeability characteristics as those of FIG. 8.

It should be noted that the laminates shown in FIGS. 8 and 9 are examples only of structures which may be used in the present invention. Laminates of the type shown in FIGS. 8 and 9 are available from Aluminum-Walzwerke Singen GmbH of Alusingen-Platz 1, D-7700 Singen/Hohentwiel, West Germany. One feature of the embodiments of FIGS. 8 and 9 is that they are relatively rigid, which helps to avoid them being damaged and makes it easier to use them in the devices shown in FIGS. 1 to 5.

It should also be noted that the seal between the lid and base laminates cannot be broken and resealed without it being evident that this has occurred so that tamper evidence is provided. This type of tamper evidence is not provided by the capsules which are conventionally used.

The powdered medicament in the blisters preferably has a particle size range of from 0.5 to 10 microns. The medicament may comprise a pharmacologically active substance, such as one or more of those mentioned above, with a pharmaceutically acceptable carrier, such as lactose or starch, in powder form.

The total amount of medicament present in each blister, including any carrier, is preferably from 20-50 mg. This quantity of powder is such that it can be inhaled by an adult patient by a single inhalation. The internal volume of each blister is preferably such that the medicament occupies only a relatively small proportion of the volume. The reason for this is to enable the blister to be emptied as completely as possible and as reproducibly as possible, the latter being important to ensure that the patient always receives substantially the same dose. As will now be explained with reference to FIGS. 10 to 13, although some powder may be left behind in the blister and not entrained by the air flow, by proper design of the blister this amount can be kept to as little as 10% of the original contents of the blister, or even less.

Figure 10:
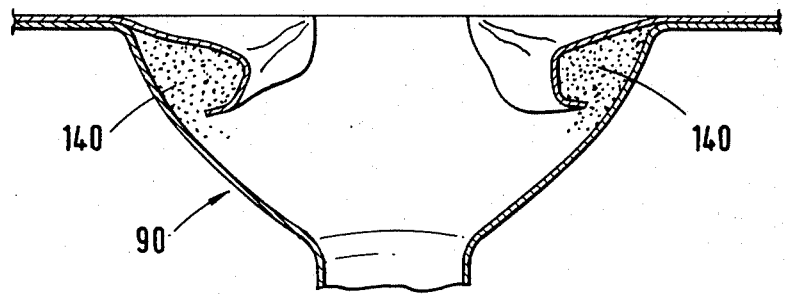
FIGS. 10 and 11 are vertical sections, on an enlarged scale, showing blisters after puncturing, in which powder has been trapped.
Figure 11:
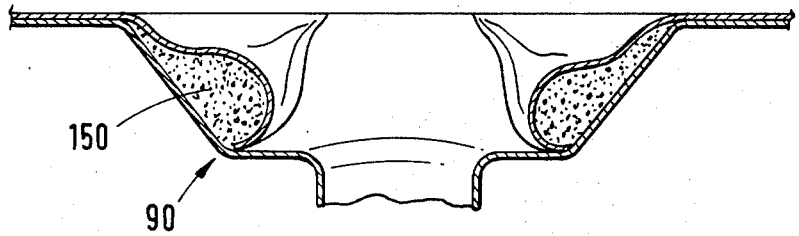
Figure 12A:
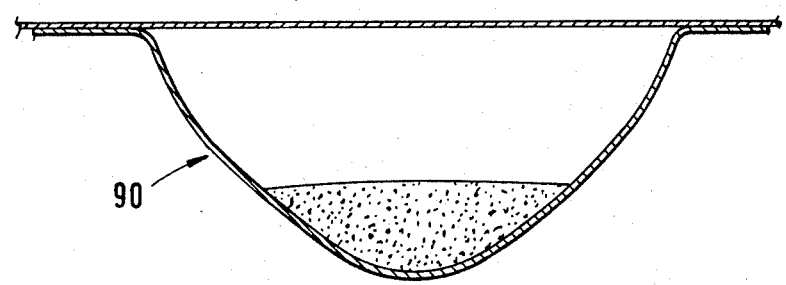
FIGS. 12a and 12b are vertical sections, on an enlarged scale showing a blister before and after puncturing.
Figure 12B:
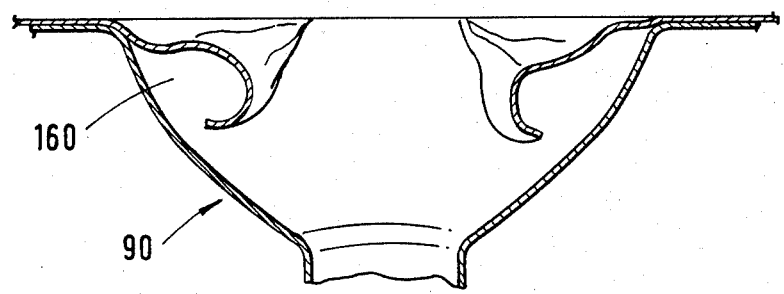

FIG. 10 shows, after puncturing a blister 91 which was overfilled with medicament, i.e. the medicament occupied too great a proportion of the volume. As can be seen, the peripheral portion of the punctured cover has trapped some of the powder in an annular region 140. FIG. 11 shows powder entrapment produced by having a blister which is too shallow, i.e. the ratio of diameter to depth is too great. Here the peripheral portion of the punctured cover traps powder in an annular region 150. FIGS. 12a and 12b, in contrast, show a blister, before and after puncturing respectively, which is neither overfilled nor too shallow. Here no powder is shown trapped in the region 160 which corresponds to the regions 140 and 150. In practice, a little powder may be trapped even in this case, but the amount will be small compared to that in regions 140 and 150.

Figure 13:
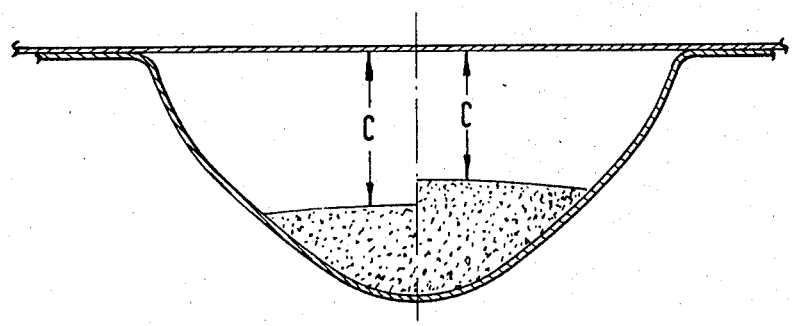
FIG. 13 is a vertical section, on an enlarged scale, showing a blister filled to two different extents with powder.

FIG. 13 indicates the filling range which is preferred in order to reduce powder entrapment caused by the mechanism of FIG. 10, whilst at the same time having enough powder to give a reproducible dose. The right hand side of FIG. 13 indicates the maximum degree of filling which may be used without significant powder entrapment. The internal depth of the blister (d in FIG. 7) is 4.5 mm and its volume is 0.2 cm$^3$. The blister contains 40 mg of powder having a bulk density of 0.5 and thus occupying a volume of 0.08 cm$^3$ (40% of the blister volume). The clearance c between the upper surface of the powder and the blister cover is 2.8mm, i.e. the depth of the powder is approximately half the depth of the blister. The left hand side of FIG. 13 illustrates a presently preferred degree of filling. Here the blister contains 25 mg of powder occupying 0.5 cm$^3$ (25% of the blister volume), and the clearance c is 2.8 mm. As a practical matter there should preferably be at least 20 mg of powder. In order to reduce powder entrapment by the mechanism of FIG. 11 the ratio of blister diameter D to blister depth d (see FIG. 7) is preferably less than 4.5:1. Typical values which may desirably be used are in the region of 2.6:1 to 2.9 to 1. The ratio is preferably not less than 2.4:1 in order to avoid problems in forming the blisters. Values of D are typically about 11 to 12 mm, and values for d are typically about 3.8 to 4.5 mm. It should also be noted that the generally conical shape of the blisters is advantageous in that it presents the medicament to the airflow through the punctured blister in such a way as to assist emptying by the airflow.

I claim:

1. A pack comprising a circular carrier disc which has a plurality of pre-filled, hermetically sealed containers formed integrally therewith and arranged in a circle, each container being of generally conical form and containing a dose of medicament in the form of an inhalable powder, each container comprising at least opposed puncturable surfaces for forming a hole through said container to allow air to flow through the container to entrain the powder contained therein.

2. A pack as claimed in claim 1, wherein the ratio of diameter to depth of each container is less than 4.5:1.

3. A pack as claimed in claim 1, wherein the ratio of diameter to depth of each container is not less than 2.4:1.

4. A pack as claimed in claim 1, wherein the carrier disc is of foil laminate material.

5. A pack as claimed in claim 4, comprising a base laminate and, secured thereto, a lid laminate in which depressions are formed to define the containers with the base laminate.

6. A pack as claimed in claim 5, in which the base laminate and lid laminate are secured to one another by a seal such that breaking and re-sealing thereof is tamper evident.

7. A pack as claimed in claim 5, wherein each of the base and lid laminate includes a layer of aluminum.

8. A pack as claimed in claim 1, wherein the medicament comprises an active ingredient selected from salbutamol and beclomethasone dipropionate.

9. A pack as claimed in claim 1, wherein the medicament comprises sodium cromoglycate.

10. A pack as claimed in claim 1, in which the particle size of the medicament is substantially in the range 0.5–10 microns.

11. A pack as claimed in claim 1, in which the medicament comprises a pharmacologically active substance admixed with a solid pharmaceutically acceptable carrier.

12. A pack as claimed in claim 1, in which each container has a volume such that the powder therein occupies not more than 40% thereof.

13. A pack as claimed in claim 12, in which the powder occupies approximately 25% thereof.

14. A pack as claimed in claim 1, in which each container contains at least 20 mg of powder.

15. A pack as claimed in claim 1, in which each container has a depth such that the depth of powder therein is not more than approximately half the depth of the container when the container is oriented so that the conical form thereof tapers downwardly.

* * * * *